US010139384B1

(12) United States Patent
Nourbakhsh (10) Patent No.: US 10,139,384 B1
(45) Date of Patent: Nov. 27, 2018

(54) DATA FUSION FOR PERSONAL AIR POLLUTION EXPOSURE

(71) Applicant: Airviz Inc., Pittsburgh, PA (US)

(72) Inventor: Illah Nourbakhsh, Pittsburgh, PA (US)

(73) Assignee: Airviz Inc., Pittsburgh, PA (US)

( * ) Notice: Subject to any disclaimer, the term of this patent is extended or adjusted under 35 U.S.C. 154(b) by 211 days.

(21) Appl. No.: 14/990,940

(22) Filed: Jan. 8, 2016

Related U.S. Application Data (60) Provisional application No. 62/104,394, filed on Jan. 16, 2015.

(51) Int. Cl.
*G01N 33/22* (2006.01)
*G01N 33/00* (2006.01)

(52) U.S. Cl.
CPC ..... *G01N 33/0075* (2013.01); *G01N 33/0022* (2013.01); *G01N 33/0062* (2013.01)

(58) Field of Classification Search
CPC .......... G01N 33/0075; G01N 33/0022; G01N 33/0062
See application file for complete search history.

(56) References Cited

U.S. PATENT DOCUMENTS

| | | | |
|---|---|---|---|
| 4,375,667 A | 3/1983 | Buchan | |
| 5,467,189 A | 11/1995 | Kreikebaum et al. | |
| 6,502,469 B2 | 1/2003 | Lawless | |
| 6,693,546 B2 | 2/2004 | Skardon | |
| 7,389,158 B2 | 6/2008 | Desrochers et al. | |
| 8,009,290 B2 | 8/2011 | Unger | |
| 8,085,145 B2 | 12/2011 | Fu et al. | |
| 8,147,302 B2 | 4/2012 | Desrochers et al. | |
| 8,150,465 B2 | 4/2012 | Zhang et al. | |
| 8,161,830 B2 | 4/2012 | Boudries et al. | |
| 8,204,786 B2 | 6/2012 | LeBoeuf et al. | |
| 8,441,635 B2 | 5/2013 | Schubert et al. | |
| 8,813,583 B2 | 8/2014 | Kilps et al. | |

(Continued)

OTHER PUBLICATIONS

U.S. Appl. No. 14/684,542, filed Apr. 13, 2015.

*Primary Examiner* — Cuong B Nguyen
(74) *Attorney, Agent, or Firm* — K&L Gates LLP (57) ABSTRACT

Systems and methods collect time and location indexed (spatiotemporal) air quality measurements for an individual and aggregate those measurements to obtain cumulative air quality exposures for the individual that are presented to the individual with an interactive graphical display. A plurality of air quality sensors each transmits air quality data to the data center. The air quality sensors can comprise both indoor and outdoor air quality sensors. The data center stores the temporally-indexed user location information and the spatiotemporally-indexed air pollution information from the air quality sensors. Based on this information, it calculates user air quality exposure measures and transmits them to a graphical display device associated with the individual so that the individual can visualize his/her pollution exposure over time. Where the data center has information on the individual's activities at certain times, it can compute and display for the individual air quality exposure measures by activity type. The calculations can use a K-nearest neighbor algorithm to compute the individual's air quality exposures.

20 Claims, 4 Drawing Sheets

(56) References Cited

U.S. PATENT DOCUMENTS

| | | | | |
|---|---|---|---|---|
| 2010/0253509 | A1* | 10/2010 | Fu | G08B 21/12 340/539.22 |
| 2010/0273665 | A1* | 10/2010 | Haick | B82Y 15/00 506/8 |
| 2014/0107932 | A1* | 4/2014 | Luna | G01D 21/00 702/19 |
| 2015/0356851 | A1* | 12/2015 | Feletti | A61B 5/0002 340/539.26 |

* cited by examiner

DATA FUSION FOR PERSONAL AIR POLLUTION EXPOSURE

PRIORITY CLAIM

The present application claims priority to U.S. provisional application Ser. No. 62/104,394 filed Jan. 16, 2015, which is incorporated herein by reference in its entirety.

BACKGROUND

Field of Invention

The present invention relates to the estimation of personal exposure to air pollution, and in particular to the characterization of cumulative exposure based on location, activity and ambient air pollution information across multiple sensor networks.

Introduction

Significant bodies of research indicate that cumulative, personal exposure to fine particulates (i.e. PM2.5) is strongly correlated with pulmonary disease and cardiovascular disease. PM2.5 is defined as the aggregate measure, by weight, of all fine and ultrafine particulate pollution in the air, with particle sizes 2.5 microns and below. PM2.5 is typically measured as micrograms per cubic meter. PM2.5 is measured in a federal regulatory manner by collecting 2.5 micron and smaller particles in a filter, then measuring the change in weight of the filter paper. Additionally, particles are counted, typically in particles per liter, by measuring the scattering of collimated light in a dark chamber off individual particles.

In addition, statistically significant correlations have now been discovered between exposure to PM2.5 by pregnant women and the onset of autism and attention deficit hyperactivity disorder in children. Thus, both for personal health and for reasons of progeny health, the comprehensive estimation of cumulative personal air pollution exposure carries significant value in enabling action by individuals to mitigate the risks of pulmonary disease, cardiac disease, asthma and numerous infant health concerns. Existing approaches to measuring personal air exposure have focused on creation of dense measurement networks in outdoor spaces and indoor space, for example using primarily vehicles as mobile air pollution measurement stations. Other prior art creates networked air quality sensors in homes to create unique fingerprints for each resident, characterizing each home's air system. However these network solutions fail to accurately measure personal exposure, because each fails to combine ambient pollution data with the activity information of a single individual in a bespoke manner. Alternatively, a second class of solutions in the state of the art concentrate on measuring air pollution exposure using personally attached, wearable devices, for examples with a personal monitor that compares ambient pollution levels to thresholds in order to generate alarms. These complex on-body systems are expensive and represent fragile single points of failure. GPS information is further fragile, working only when the signal has clear satellite line of sight and therefore failing to provide contextual information in indoor spaces and in dense urban spaces or even in narrow valleys. Furthermore the state of the art fails to combine personal air pollution exposure data with multi-sensor information regarding personal location, personal activity and personal annotation.

SUMMARY

In one general aspect, the present invention is directed to systems and methods for collecting time and location indexed (spatiotemporal) air quality measurements for an individual and aggregating those measurements to obtain cumulative air quality exposures for the individual that can be presented to the individual with an interactive graphical display. User location data for the individual is transmitted electronically to a data center (that has one or more computer servers). The user location data could be from a network-enabled, wearable activity tracker device with a GPS sensor or a WiFi-enabled mobile computer device whose location is tracked through WiFi network access points, for example. A plurality of air quality sensors each transmits air quality data to the data center. The air quality sensors can comprise both indoor and outdoor air quality sensors. The indoor one(s) can be located in the individual's home (or other building of interest to the individual), and the outdoor sensors can be government, municipal or otherwise public air quality measurement units whose data are accessible from online databases.

The data center stores the temporally-indexed user location information and the spatiotemporally-indexed air pollution information from the air quality sensors. Based on this information, it calculates air quality exposure measures for the individual and transmits them to a graphical display device associated with the individual so that the individual can visualize his/her pollution exposure over time. Further, where the data center has information about the individual's activities at certain times of the day (e.g., working, exercising, etc.), it can display for the individual's air quality exposure measures by activity type. The calculations can use algorithms, such as a K-nearest neighbor algorithm to compute the individual's air quality exposures from the vast amounts of air quality measurement data.

FIGURES

Various embodiments of the present invention are described herein in conjunction with the following figures, wherein.

DETAILED DESCRIPTION

In one general aspect, the present invention uses artificial intelligence (AI) machine learning clustering, classification and data fusion techniques to robustly measure and categorize personal air pollution exposure. Such algorithms include K-nearest neighbor clustering of GPS locations and time indexed as a hashed pair, to identify place and location pairings for cumulative exposure sums.

A cloud-based Internet data server aggregates air pollution data that is spatially and temporally labeled across multiple data source types. The present embodiment can incorporate all AirNow Environmental Protection Agency national air quality data, using the AirNow A.P.I. to mirror all posted information to the aforementioned server. Furthermore, the present embodiment can mirror all data posted by other public air quality monitors, such as from local government health departments. Municipal air quality monitors are, by law, open data, and one skilled in the field will appreciate instantiation of the invention's data mirroring technique at the national scale.

Indoor, publicly available air quality monitoring stations are a nascent, quickly growing body of sensors. Just as AirNow and health department sensors are geolocated, so all publicly available indoor air quality measurement sensors are also geolocated, enabling mirroring with spatial and temporal indices. Extant sensors used include: Hach Met-One HHPC-6, Dylos 1100P, Thermo Scientific 1405-F TEOM, the Met-One BAM-1020, and the Speck from AirViz.

The server further supports OAuth authentication and can use a Node.js database structure, enabling the storage and retrieval of both public and private information. Thus, for each user, their authenticated set of additional, personal air quality monitors will also generate data that is stored and directly accessible, whether from indoor monitors in residences, in workplaces, or wearable monitors positioned, for instance, on the wrist.

The server further stores all contextual information suitable for data fusion, including user location information, user activity biometric information and related context taken from data services provided by the user's mobile devices. Mobile phones, tablets, laptops and wearable biometric devices including Fitbit and Jawbone Up are all capable now and in the near future of providing location information and activity information by making use of Wifi mapping techniques, cellular signal triangulation of numerous other infrastructure-based techniques combined with local annotation and accelerometer information. Thus for each use the server can map user location and activity directly to the closest possible estimate of air pollution exposure for each time increment. External data sources such as the Allegheny Count Health Department TEOM equipment publishes a public interface for accessing GPS coordinates of sensors and time-stamped air pollution readings. This is one example of outdoor exposure data that this invention directly employs.

Such information, providing not only geospatial data but also data regarding exercise, sleep health and work/home patterns, provides a wealth of data types for categorization of air pollution exposure.

Finally, the user input device, using native applications and a configured web URL, can provides the user with the ability to label or annotate various time spans with an annotation that will have relevance for the categorization and review of overall exposure at a later time. Such annotations include user-designed triggers such as asthma inhaler usage, shortness of breath, arrhythmia, smell episodes, headaches.

The server can, on a user-by-user basis, agglomerate air pollution exposure by location and by activity and state context, storing the data using a multi-resolution pyramid at varying levels of spatial and temporal resolution. With such categorization of cumulative exposure by place, time and activity in place, the user interactively explores the fused dataset over time and space, gaining an authentic intuition for how air pollution accumulation varies between ritual aspects of activities of daily life, and between places and activities. For example the user can quantitatively evaluate the overall pollution exposure at home, in the bedroom, as compared to the exposure outside of home, during commute time and workplace time, evaluating the urgency of placing an air purifier at home versus purchasing a HEPA filter for the car, or a small-enclosure purifier for the work office. Additionally, by providing annotations regarding events likely to have causal relationships to poor air quality, the user is able to visualize and test hypotheses regarding the relationship of quantitative air quality exposure to the onset of symptoms such as shortness of breath.

Figure 1:
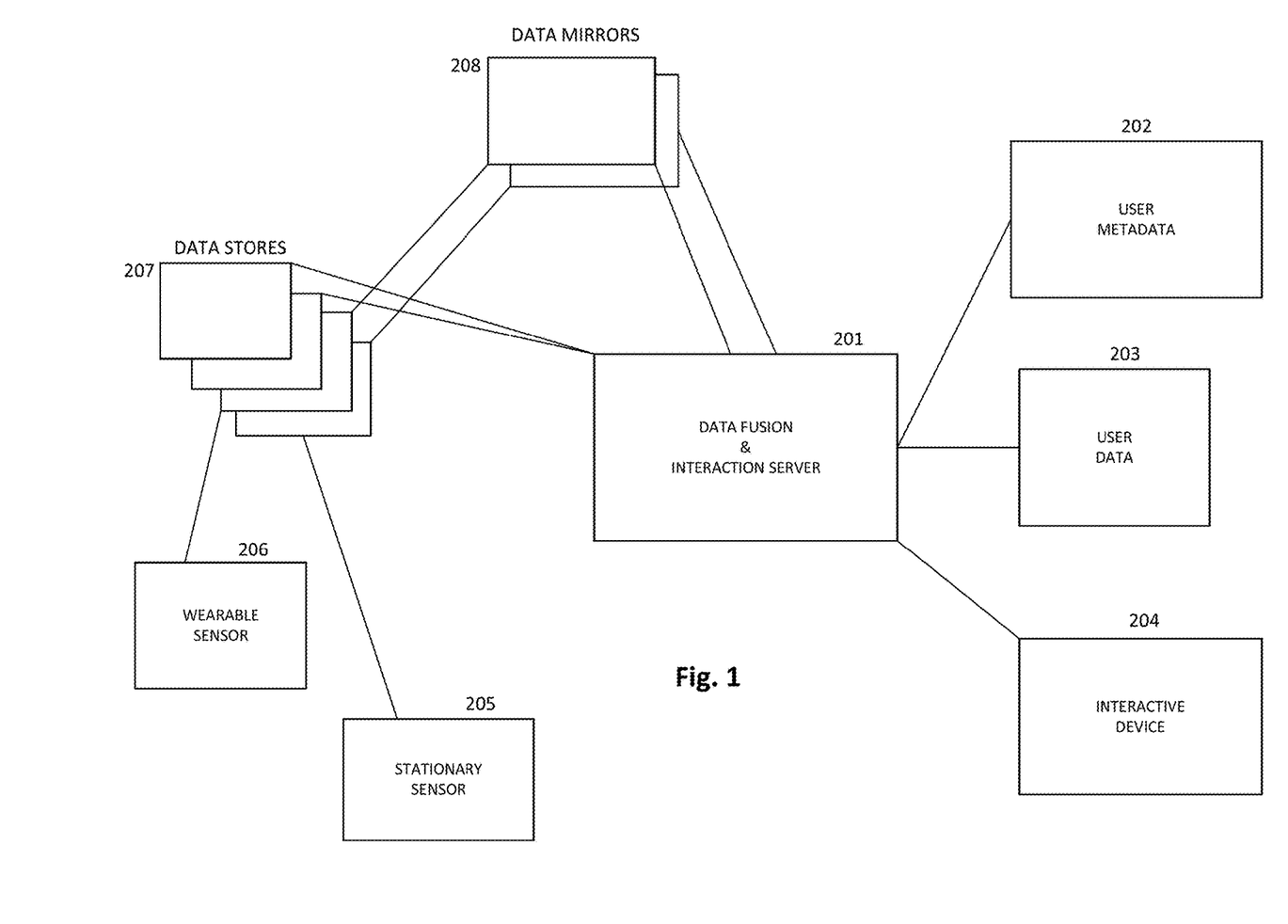
FIG. 1 is diagram of a data fusion system according to various embodiments of the present invention.

FIG. 1 illustrates an embodiment of the data fusion system, demonstrating how the system combines air quality information, biometric data, location information and activity information into an interactive visualization of annotated, personal air pollution exposure over time and space.

The data fusion and interaction server system 201 performs on-line data fusion computational processing and interactive serving of personal air pollution exposure visualization and categorization using on-line communication protocols (e.g. HTTPS with OAuth authentication). User Metadata 202 stores authentication, credentials and unique identification information for each system user. User Data 203 stores fused, pre-computed data regarding individuated user air pollution exposure over time and space as well as user air pollution cumulative exposure by category of location and activity. Interactive GUI device 204 provides direct interaction affordance to a user by being served by Server 201. Handheld Internet-connected devices and desktop devices, including Android and iPhone tablets, phones and laptops that connect and offer direct data interaction are instances of Interactive GUI Device 204. Wearable sensor 206 collects air pollution, biometric, activity, and/or location information directly on the user's body. Various Fitbit, Jawbone Up and BodyMedia wearable systems can instantiate Wearable Sensor 206. Stationary sensor 205 collects air pollution and activity information at a fixed location, such as a home wall or building roof. NEST indoor sensors, Netatmo sensors, the Speck® air quality monitor from Air Viz, and municipal air quality sensors are examples of the Stationary Sensor 205. Data Stores 207 store temporally tagged environmental, biometric and activity data from both Wearable Sensors 206 and Stationary Sensors 205. Data Mirrors 208 are populated with data regularly by fusing, interpreting and re-saving Data Stores 207. The Data Fusion and Interaction Server 201 is capable of accessing relevant user and contextual data both from original Data Stores 207 and from Data Mirrors 208.

Numerous wearable sensors collect, store and communicate information regarding a user's biometric data, environmental context and activity data. Such data includes heart rate, heart rate variability, GPS location, Wifi-based location, galvanic skin response, exercise start and stop times, exercise intensity, calorimetric counting, cumulative UV exposure, sleep quality, deep sleep start and stop times, local air pollution measurements, and associated values. Wearable devices report values to corporate data stores, some cases providing public interfaces for data extraction, such as Jawbone UP, and in other cases providing only non-real-time review of data at slow data rates, such as BodyMedia sensors. Mobile phones and tables such as Android devices and iPhones provide user location and user activity information directly and through executing local applications (i.e. App's). Such App's also enable the user to directly annotate context, and this manually inserted information is stored in Data Stores using the same storage and retrieval architecture and sensor-collected information. Remote access demands user-based authentication, using corporate authentication or using third-party identity verification using services such as Facebook and Google. Direct, real-time access of data stores (207) when appropriate are thus enabled by the Data Fusion Server (201) using user authentication credentials which are entered initially by users via an Interactive Device (204) such as an iPhone, and then stored as encrypted User Metadata (202). In the case of data stores without high-efficiency Application Program Interfaces for direct, high-bandwidth data access (such as NEST home monitors), Data Mirrors (208) duplicate, process and re-save Data Store information on alternative databases architected for Interaction Server's high-rate data posting processes. In one embodiment, Data Mirrors make use of MySQL for metadata structural information and Node.js for real-time insertion and extraction of data at a nearly unlimited resolution and size scale. In order to regularly access corporate Data Stores, Data Mirror mirroring algorithms use User Metadata (202) authentication credentials by requesting such credentials from the Data Fusion server (201).

Numerous stationary sensors (205) provide activity and environmental information. NEST provides user activity information, user location information, temperature carbon monoxide and carbon dioxide level information. Netatmo provides air quality information, temperature and humidity information. Another suitable stationary sensor is the Speck® air quality monitor from Air Viz. More details about such air quality monitors can be found in (1) U.S. patent application Ser. No. 14/684,542, entitled "Air Quality Sensor," filed Apr. 13, 2015 and (2) U.S. patent application Ser. No. 62/189,978, entitled "Group Calibration of Air Quality Monitors," filed Jul. 8, 2015, both of which are incorporated herein by reference in their entirety. In a manner identical to that of Wearable Sensors, such stationary sensor information is stored off-board, in on-line Data Stores and is available for authenticated extraction, in some cases with sufficient efficiency for real-time, direct use by the Interaction Server and in other cases with insufficient efficiency, thus requiring implementation of a Data Mirror via authentication credentials provided by the relevant user and stored in User Metadata.

User Metadata (202) stores both direct authentication and contact information for the Personal Air Pollution Exposure interaction system, as well as authentication keys for all data stores relevant to each individual user's air pollution exposure, including their wearable sensors and the stationary sensors within their authentication scope and within their vicinity. Such metadata is stored with appropriate encryption controls to dissuade nefarious access and to protect the privacy and data rights of all system users.

Date Fusion and Interaction Server (201) provides authentication services for data mirroring, and also performs data fusion to yield annotated and classified data regarding cumulative air pollution exposure per-user. Using K Nearest Neighbor automatic clustering techniques, the Server groups together air pollution exposure readings by location, local calorimetric expenditure, sleep/wake fluency, exercise and exercise type, and user annotations. The Server computed, organizes and presents classified cumulative air pollution exposure values both in real time, as required for custom views by the Interactive Device (204), and as pre-computed results stored as User Data (203) to enable high-speed visualization and recall by the user, also through an Interactive Device (204). As one example, the user may log into the air pollution exposure system, being verified in identity via stored User Metadata, and then may visualize cumulative 2.5 micron particulate air pollution exposure over the past one month period by home and school categories. Furthermore, home air pollution exposure may be broken out into two cumulative values, one for exposure during sleep in the child's bedroom and a second for exposure during waking hours. Finally, user-annotated episodes of asthma attacks requiring inhaler doses may be shown for each of school and home categories. Such visualization affords the child's parents the ability to understand what fraction of total particulate exposure sustained by the child is due to each portion of the ritual week, and therefore what corrective actions will maximize reduction of particulate exposures that trigger asthma attacks and, thereby, poorer quality of life.

Pre-computing of such frequently requested categorizations and pre-saving of such data as User Data (203) minimize the wait time when the user makes a real-time request using an Interactive Device (204). However, it is not possible to pre-compute and store all possible data classification visualizations ahead of time. Thus the Server (201) must afford both the submission of interactive, pre-computed data as well as real-time data fusion using Data Stores and Data Mirrors as appropriate for user visualization requests.

The Interactive Device (204) functions as the principal communication link between a user and the air pollution exposure information available through the invention. The user inputs login information, contact information, credentialing information and authenticates connections to extant data services such as those provided by wearable and stationary environmental and activity sensors. All these specifications are performed using one or more Interactive Devices connecting to the Interaction Server 201. Such Interactive Devices include mobile devices through App links, browser-based secure https: links and native applications on computing devices. The user also uses Interactive Devices to provide annotations directly to the personal air pollution exposure system. This data, stored directly as User Data (203), is immediately available during visualization of air pollution exposure, both as a tertiary annotation field and as additional categories for organizing cumulative air pollution exposure. For example a manually user-entered annotation regularly marking days when a residence has distinct industrial smells from nearby manufacturing plants enables the user to organize personal exposure by showing cumulative air pollution on days so marked as compared to all other days over the past month. Such visualization would enable the user to understand whether strong industrial smell is likely to correlate with poor air pollution that leads to clearly deleterious health consequences in the long term.

The Interactive Device component also serves as the principal means by which the user creates interactive, explorable visualizations of fused data in order to comprehend cumulative air pollution exposure. Data Mirrors and User Data architectures pre-compute air pollution values indexed spatially and temporally, and insert pyramidally arranged coarse-resolution versions of all such data, enabling the Interaction Server to request and receive air pollution exposure data at exactly the resolution demanded for the specific temporal and spatial window specified by the user through the Interactive Device. This resolution match between required and recorded data maximizes the speed with which a user can request, modify and observe patterns in data across time and space without waiting for regeneration and resampling computations to take place at the server.

The following use case presents an example for an individual with exercise-induced asthma who needs to understand air pollution exposure by location and by activity. The individual is wearing a Jawbone UP bracelet, has installed a single indoor PM2.5 air quality sensor in the bedroom, works at an office building with PM2.5 air quality sensors in the building, and lives in an urban area where outdoor air quality is published by the E.P.A. The server collects a data mirror of outdoor air quality in the individual's city of residence, and also collects time-indexed air pollution data from both the residence sensors and the workplace building sensors. The individual annotates specific repeating time ranges as 'work time' directly, and the Jawbone UP provides activity information labeled temporally, including sleep and waking time, and exercise type and time. The server combines all the above data sources to present the individual with hour-by-hour and cumulative air pollution exposure values on an interactive screen. The server accomplishes this data fusion by conducting data classification, indexed by GPS locations of static air pollution sensor devices, subtracted from estimated GPS location readings of the individual. Clustering yields time-indexed air pollution readings likeliest to represent true exposure by the individual, and indexed further by type of activity and by location. The resulting data is stored both as selected data points and as cumulative air pollution values, represents as a sum of data points over time, pre-computed to increasingly coarse temporal resolution using a resolution pyramid for pre-storage and fast access.

A summary of total weekly pollution exposure is presented by activity type. The individual sees that 25% of total air pollution exposure accumulates during sleep time in the bedroom, but that five time greater air pollution exposure accumulates during daily jogging than is proportional to time spent jogging. The individual notes that disproportionately little air pollution exposure accumulates during the workday. The individual concludes that the workplace HVAC system is functioning well and likely not inducing asthma; however that bedroom exposures warrant purchase of an air purification in-room system, and that, most importantly, jogging locations and times need to be re-thought to mitigate exposure during exercise.

In various embodiments, systems and methods for measuring and interactively visualizing the air pollution exposure of an individual may be provided. The system or method may comprise: associating an individual's time-indexed location information with spatially nearby time-indexed air pollution information to yield time-indexed, location-indexed air pollution exposure information specific to the individual; and interactively presenting cumulative air pollution exposure information to the individual, operable to vary the spatial and temporal resolution of air pollution exposure data, to select air pollution exposure readings and cumulative values across temporally specified and location-specified subwindows.

The system and methods may also include one or more of the following features, in any reasonable combination:
  Integration of location information to specifically select from indoor air pollution sensor readings and outdoor air pollution sensor readings to do the data fusion.
  Specifically measuring & visualizing PM2.5 (weight).
  Specifically measuring & visualizing particulate count values.
  User annotates the data which annotation can be used for classification and visualization.
  Associate an individual's time-indexed behavior activity information with time-indexed exposure information to yield interactive visualization of cumulative air pollution exposure by activity type and location.

Figure 2:
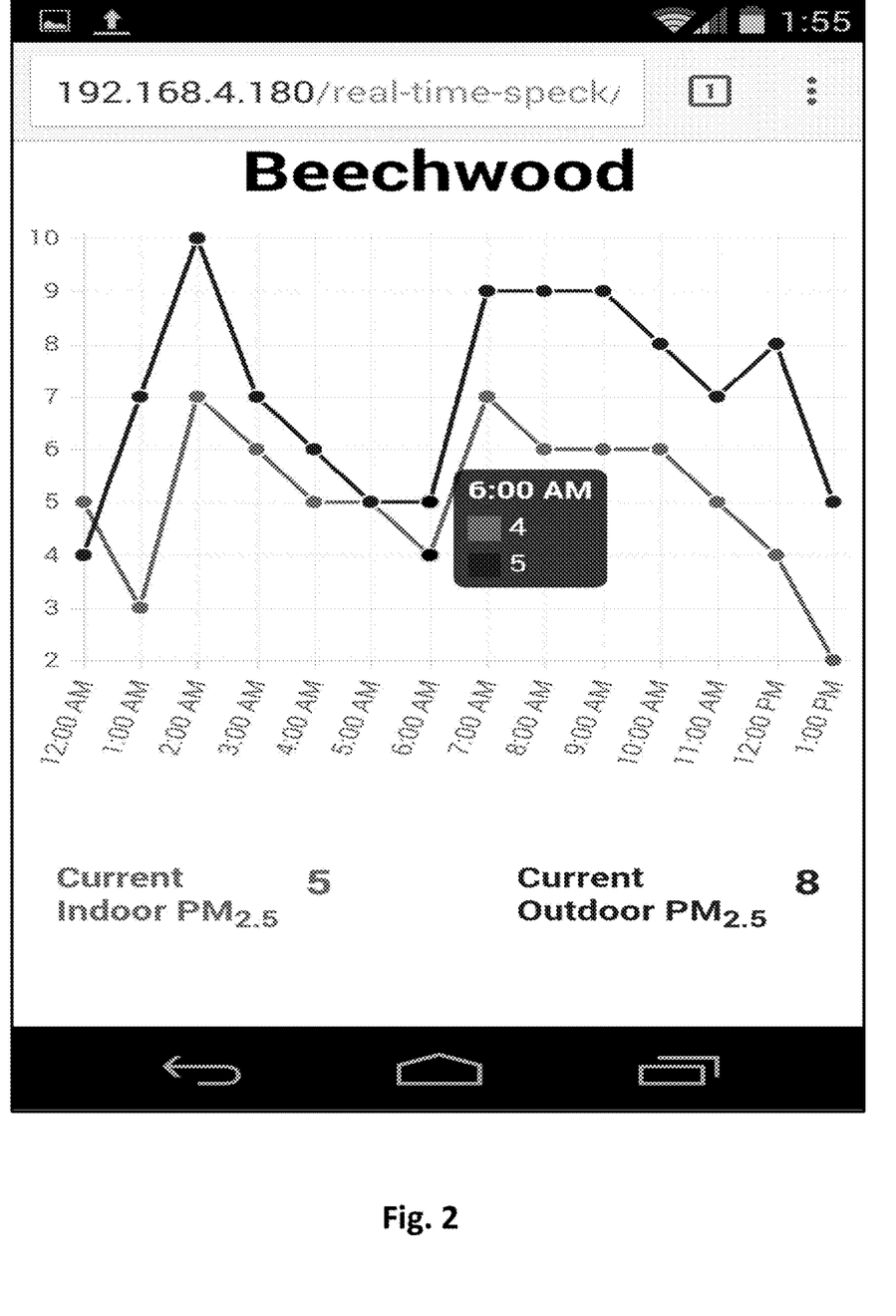
FIGS. 2 and 3 are sample displays of the graphical user interface tracking particle concentration over time for various example locations according to various embodiments of the present invention.
Figure 3:
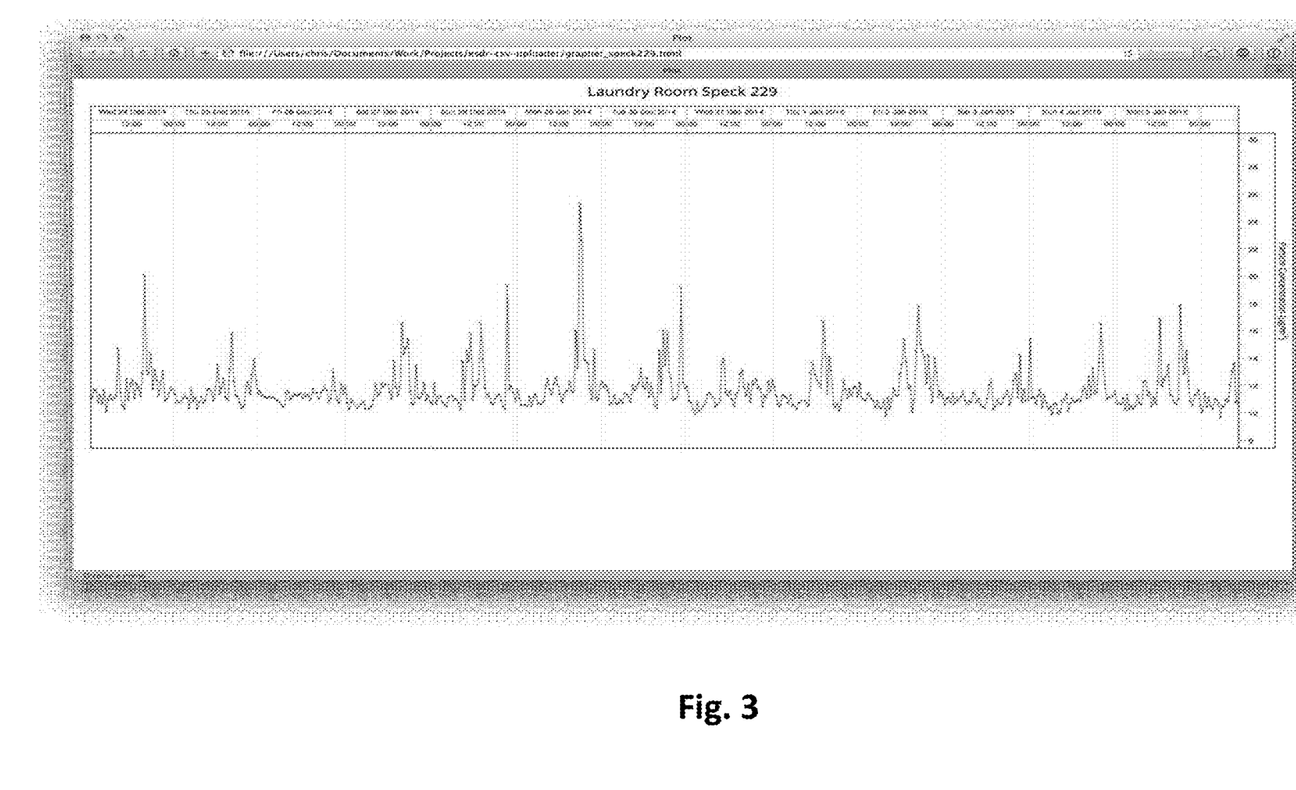

FIGS. 2 and 3 provide examples of tracking particle concentration over time in accordance with various embodiments of the invention. FIG. 2 shows hourly indoor and outdoor readings (PM2.5) from respective indoor and outdoor sensors over time (a 14-hour time window) at a particular location ("Beechwood"). FIG. 3 shows continuous an air pollution measures ($\mu g/m^3$) for a particular home location (the laundry room) over a two-week time period.

Figure 4:
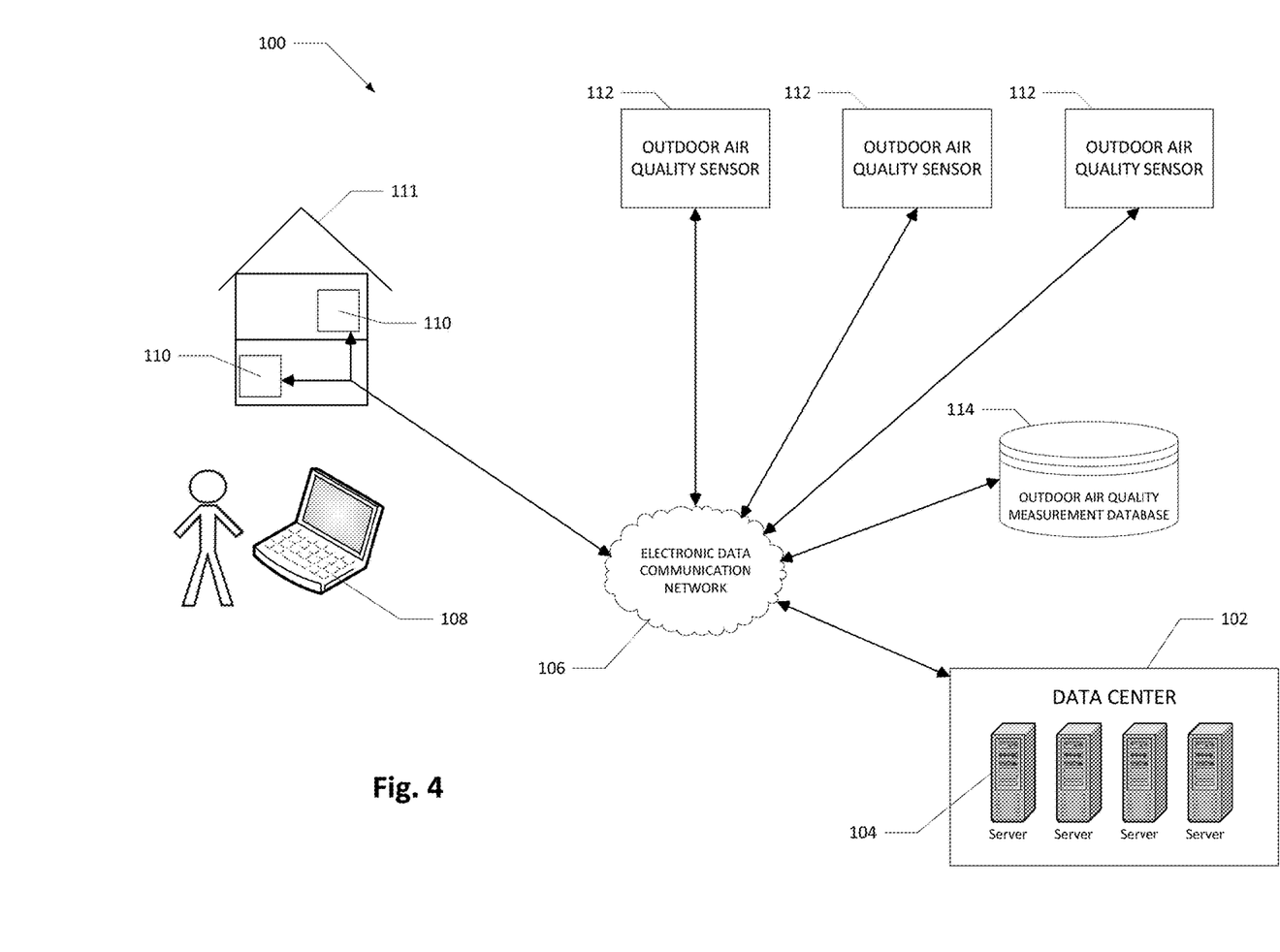
FIG. 4 is a diagram of a data system for computing a user's air quality measures according to various embodiments of the present invention.

In one general aspect, therefore, the present invention is directed to a system for measuring and viewing air pollution exposure for a user. As shown in FIG. 4, the system 100 comprises a data center 102 that comprises one or more computer servers 104, such as the data fusion and interaction server 201 described above. The system also comprises means, associated with the user, for communicating user location data to the data center 102 via a computer network 106. The user location means could be, as described above, a network-enabled, wearable activity tracker device 206 with a GPS sensor (see FIG. 1), a WiFi-enabled mobile computer device 108 (e.g., laptop, smartphone, tablet, etc.) where the location of the WiFi network's access point is used to determine the user's location, and any other suitable location or GPS device. The computer network 106 can comprise the Internet, WiFi networks, LANs, WANs, etc. The system 100 also comprises a plurality of air quality sensors that each transmits air quality data to the data center 102 via the computer network 106. The plurality of air quality sensors can comprises one or more air quality sensors 110 in the user's home 111 (or other building of interest to the user) and one or more outdoor air quality sensors 112 that are not located in the user's home (or other building of interest to the user). The air quality measures from the sensors 110, 112 could be PM2.5 air quality data, for example. As mentioned previously, the data from the outdoor air quality sensors 112 may be stored in one or more online databases 114, and the data center 102 can access the air quality measurement data stored in the database 114 via an API. The system also comprises a graphical display device that is in communication with the data center via the computer network. The graphical display device may be the display on the user's computer device 108 or a display on one of the user's home air quality sensor devices 110, or any other suitable graphical display device.

As described above, the servers 104 of the data center 102 can be programmed to store temporally-indexed location information of the user based on the user location data received from the means for communicating user location data to the data center 102. The servers 104 of the data center 102 are also programmed to store spatiotemporally-indexed air pollution information based on the air quality data received from the plurality of air quality sensors 110, 112. That is, the servers store air pollution information from the air quality sensors 110, 112 that is indexed both in terms of location (e.g., GPS coordinates) and time. The servers 104 of the data center 102 are also programmed to calculate user air quality exposure measures based on at least the temporally-indexed user location information and the spatiotemporally-indexed air pollution information, such as by using the K-nearest neighbor algorithm described above. The data center can transmit the calculated user air quality exposure measures to the graphical display device 108 for display by the graphical display device 108 via the network 106. For example, the data center 102 could compute and transmit accumulated air quality exposure measures for the user that are accumulated over a time period (e.g., day, week, month, etc.).

In various implementations, the graphic display device that displays the user air quality exposure measures comprises an interactive graphical display (e.g., one where the user can select a point of interest in the display for more detail). Such a graphical display device could comprise a personal computer, a laptop, a smartphone, a table computer, a wearable computer device, etc. Also, the data center 102 can receive user activity type annotations from the graphical display device 108 via the computer network 106 (e.g., time spent exercising, time spent a work, etc.). The data center can store the temporally-indexed user activity type annotations, and the user air quality exposure measures calculated (and transmitted) by the data center 102 can be computed based on these temporally-indexed user activity type annotations. Further, the graphical display device can display the user air quality exposure measures by activity type.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, user interface layouts, or screen displays described herein are necessarily intended to limit the scope of the invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

In various embodiments of the present invention, a single component may be replaced by multiple components, and multiple components may be replaced by a single component, to perform a given function or functions. Except where such substitution would not be operative to practice embodiments of the present invention, such substitution is within the scope of the present invention. Any of the servers described herein, for example, may be replaced by a "server farm" or other grouping of networked servers (e.g., a group of server blades) that are located and configured for cooperative functions. It can be appreciated that a server farm may serve to distribute workload between/among individual components of the farm and may expedite computing processes by harnessing the collective and cooperative power of multiple servers. Such server farms may employ load-balancing software that accomplishes tasks such as, for example, tracking demand for processing power from different machines, prioritizing and scheduling tasks based on network demand, and/or providing backup contingency in the event of component failure or reduction in operability.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

The various processes and techniques described herein may be implemented at least in part by software, comprising instructions that are stored or maintained by the computer-readable memory of the access device, the host computing device, and/or of any other device, or by independent computer-readable memory that is used for storing and transferring the software.

Although the flow charts and methods described herein may describe a specific order of execution, it is understood that the order of execution may differ from that which is described. For example, the order of execution of two or more blocks or steps may be scrambled relative to the order described. Also, two or more blocks or steps may be executed concurrently or with partial concurrence. Further, in some embodiments, one or more of the blocks or steps may be skipped or omitted. It is understood that all such variations are within the scope of the present disclosure.

What is claimed is:

1. A system for measuring and viewing air pollution exposure for a user, the system comprising:
   a data center comprising one or more computer servers;
   means, associated with the user, for communicating user location data to the data center via a computer network;
   a plurality of air quality sensors that each transmit air quality data to the data center via the computer network; and
   a graphical display device that is in communication with the data center via the computer network, the graphical display device displaying a user interface for annotating an activity type according to time;
   wherein the data center is programmed to:
      receive the activity type from the graphical display device via the computer network;
      receive the user location data from the means for communicating user location data to the data center, the user location data indexed in terms of time;
      receive the air quality data from the plurality of air quality sensors, the air quality data indexed in terms of location of each of the air quality sensors and time;
      calculate user air quality exposure measures for the activity type based on at least the air quality data for the location and time corresponding to the user location data; and
      transmit the calculated user air quality exposure measures to the graphical display device for display by the graphical display device according to the activity type and the user location data.

2. The system of claim 1, wherein:
   the user interface comprises an interactive graphical user interface; and
   the user air quality exposure measures transmitted to the graphical display device are displayed on the interactive graphical user interface.

3. The system of claim 1, wherein the graphical display device comprises a network-enabled computer device that is selected from the group consisting of a personal computer, a laptop, a smartphone, a table computer, and a wearable computer device.

4. The system of claim 1, wherein:
   the data center additionally stores the annotations for each activity type.

5. The system of claim 4, wherein the graphical display device displays the user air quality exposure measures for each activity type annotated by the user.

6. The system of claim 1, wherein the means for communicating user location data to the data center comprises a network-enabled, wearable activity tracker device with a GPS sensor.

7. The system of claim 1, wherein the means for communicating user location data to the data center comprises a WiFi-enabled mobile computer device.

8. The system of claim 1, wherein the plurality of air quality sensors comprise:
   at least one indoor air quality sensor located in a domicile of the user; and
   a plurality of outdoor air quality sensors.

9. The system of claim 8, wherein:
   the at least one indoor air quality sensor reports PM2.5 air quality data to the data center;
   the plurality of outdoor air quality sensor reports PM2.5 air quality data to the data center; and
   the data center computes the user air quality exposure measures based on the PM2.5 air quality data from both the at least one indoor air quality sensor and the plurality of outdoor air quality sensors.

10. The system of claim 1, wherein the data center computes the user air quality exposure measures using a K-nearest neighbor algorithm.

11. The system of claim 1, wherein the user air quality exposure measures comprise accumulated air quality exposure measures that are accumulated over a time period.

12. A system for measuring and viewing air pollution exposure for a user, the system comprising:
   a data center comprising one or more computer servers;
   means, associated with the user, for communicating user location data to the data center via a computer network;
   a plurality of air quality sensors that each transmit air quality data to the data center via the computer network, wherein the plurality of air quality sensors comprise:
      at least one indoor air quality sensor located in a domicile of the user; and
      a plurality of outdoor air quality sensors; and
   a graphical display device that is in communication with the data center via the computer network, wherein the graphical display device comprises an interactive graphical display for annotating an activity type according to time, and wherein the data center is programmed to:
receive the activity type from the graphical display device via the computer network;
receive the user location data from the means for communicating user location data to the data center, the user location data indexed in terms of time;
receive the air quality data from the plurality of air quality sensors, the air quality data indexed in terms of location of each of the air quality sensors and time;
calculate user air quality exposure measures for the activity type using a K-nearest neighbor algorithm based on at least the air quality data for the location and time corresponding to the user location data; and
transmit the user air quality exposure measures to the graphical display device for display by the graphical display device according to the activity type and the user location data, and
wherein the graphical display device displays the user air quality exposure measures on the interactive graphical display.

13. The system of claim 12, wherein:
the data center additionally stores the annotations for each activity type.

14. The system of claim 13, wherein the graphical display device displays the user air quality exposure measures for each activity type annotated by the user.

15. A method for measuring air pollution exposure for a user, the method comprising:
receiving, via a computer network, by a data center that comprises one or more computer servers, user location data for the user, the user location data indexed in terms of time;
receiving, via the computer network, by the data center, an activity type from a graphical display device displaying a user interface for annotating the activity type according to time;
receiving, via the computer network, by the data center, air quality data from a plurality of air quality sensors, the air quality data indexed in terms of location of each of the air quality sensors and time;
calculating, by the data center, user air quality exposure measures for the activity type based on at least the air quality data for the location and time corresponding to the user location data; and
transmitting, by the data center, the user air quality exposure measures to the graphical display device via the computer network for display by the graphical display device according to the activity type and the user location data.

16. The method of claim 15, further comprising:
storing, by the data center, the annotations for each activity type.

17. The method of claim 15, wherein the plurality of air quality sensors comprise:
at least one indoor air quality sensor located in a domicile of the user; and
a plurality of outdoor air quality sensors.

18. The method of claim 17, wherein:
the at least one indoor air quality sensor reports PM2.5 air quality data to the data center;
the plurality of outdoor air quality sensor reports PM2.5 air quality data to the data center; and
the data center computes the user air quality exposure measures based on the PM2.5 air quality data from both the at least one indoor air quality sensor and the plurality of outdoor air quality sensors.

19. The method of claim 15, wherein the data center computes the user air quality exposure measures using a K-nearest neighbor algorithm.

20. The method of claim 15, wherein the user air quality exposure measures comprise accumulated air quality exposure measures that are accumulated over a time period.

* * * * *